(12) United States Patent
Gulachenski

(10) Patent No.: US 6,544,217 B1
(45) Date of Patent: Apr. 8, 2003

(54) GUIDEWIRE-OCCLUDED BALLOON CATHETER

(75) Inventor: Joseph A. Gulachenski, Rancho Santa Margarita, CA (US)

(73) Assignee: Micro Therapeutics, Inc., San Clemente, CA (US)

( * ) Notice: Subject to any disclaimer, the term of this patent is extended or adjusted under 35 U.S.C. 154(b) by 0 days.

(21) Appl. No.: 09/494,970

(22) Filed: Jan. 31, 2000

Related U.S. Application Data

(60) Provisional application No. 60/118,390, filed on Feb. 1, 1999.

(51) Int. Cl.[7] ............................................. A61M 29/00
(52) U.S. Cl. .................................................... 604/96.01
(58) Field of Search ........................ 604/96.01, 97.01, 604/97.02, 93.01, 101.01, 104; 606/191

(56) References Cited

U.S. PATENT DOCUMENTS

| | | | | |
|---|---|---|---|---|
| 4,896,669 A | * | 1/1990 | Bhate et al. .............. 604/103.1 |
| 5,002,559 A | * | 3/1991 | Tower ......................... 600/585 |
| 5,209,727 A | * | 5/1993 | Radisch et al. .............. 604/913 |
| 5,328,468 A | * | 7/1994 | Kaneko et al. ............ 604/103.1 |
| 5,397,305 A | * | 3/1995 | Kawula et al. .............. 604/103 |
| 5,514,092 A | * | 5/1996 | Forman et al. ......... 604/101.03 |
| 5,549,580 A | * | 8/1996 | Diaz .......................... 600/585 |
| 5,618,266 A | * | 4/1997 | Liprie ............................ 600/3 |
| 5,681,336 A | * | 10/1997 | Clement et al. .......... 604/96.01 |
| 5,693,015 A | * | 12/1997 | Walker et al. ............... 604/523 |
| 6,051,607 A | * | 4/2000 | Greff ........................ 424/78.08 |

* cited by examiner

*Primary Examiner*—Teresa Walberg
*Assistant Examiner*—Daniel Robinson
(74) *Attorney, Agent, or Firm*—Burns, Doane, Swecker & Mathis L.L.P.

(57) ABSTRACT

A balloon catheter having a proximal end and a distal end and a main axial lumen extending therebetween is provided with an inflation seal such that the presence of a guidewire in the inflation seal forms a fluid-tight seal for retaining fluid in the balloon and causing inflation thereof. The inflation seal can be formed distally of the balloon or within the balloon. Marker bands disposed at the distal end a formed integrally with the structure of the balloon catheter.

7 Claims, 3 Drawing Sheets

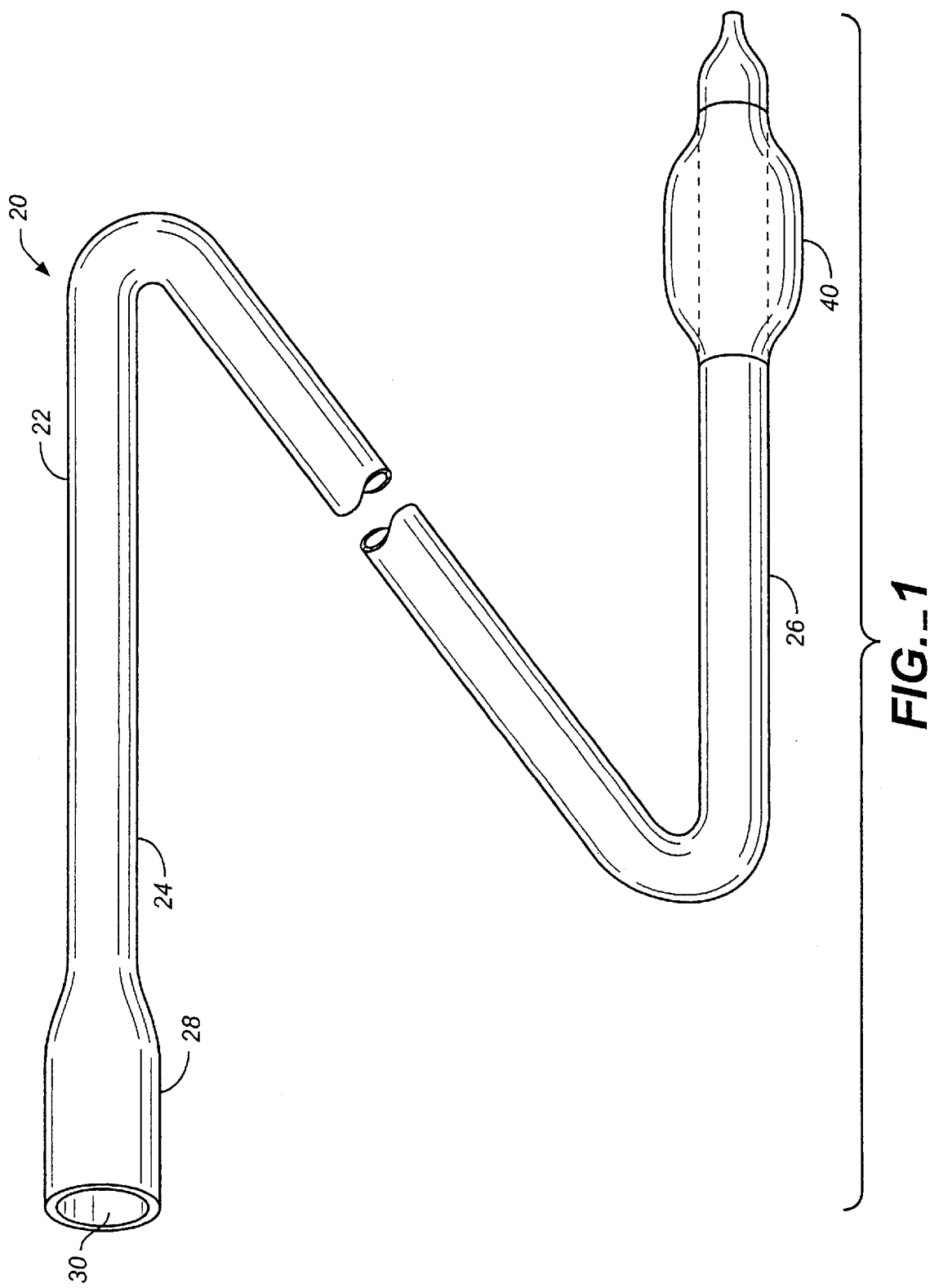
FIG._1

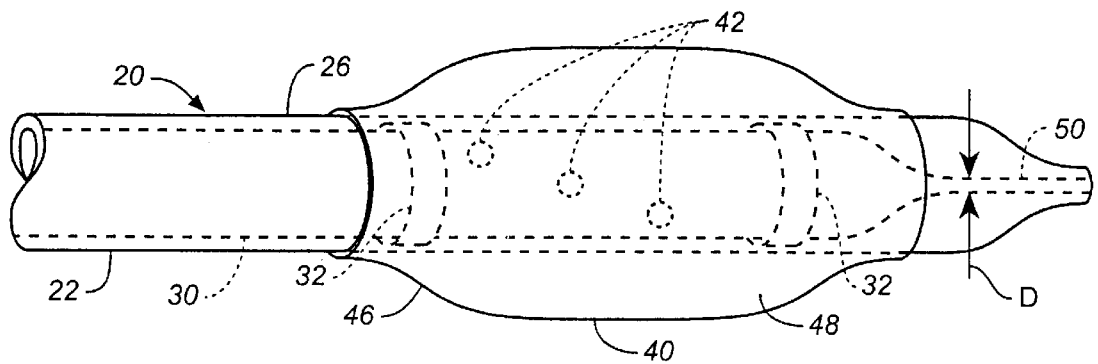
FIG._2
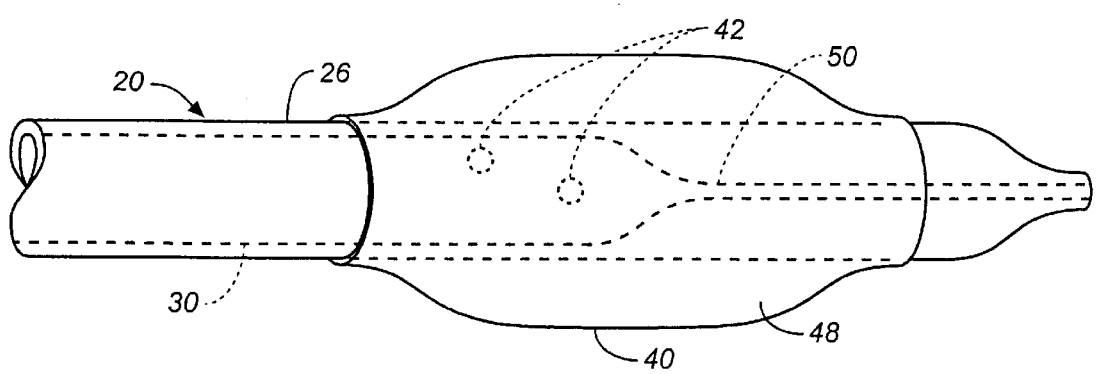
FIG._3

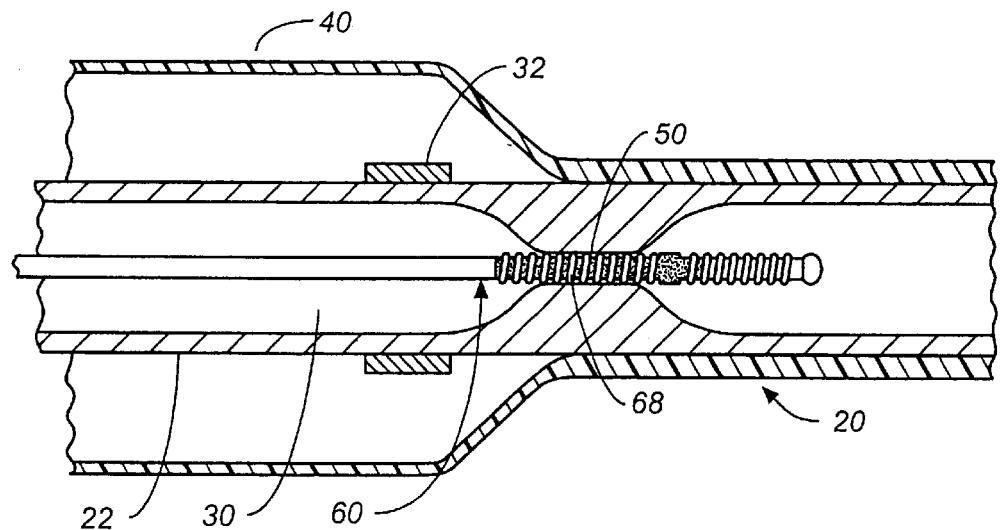
FIG._4
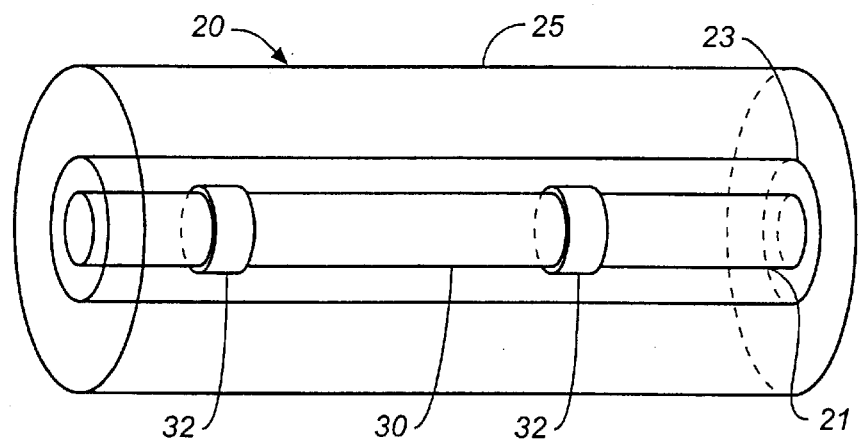
FIG._5
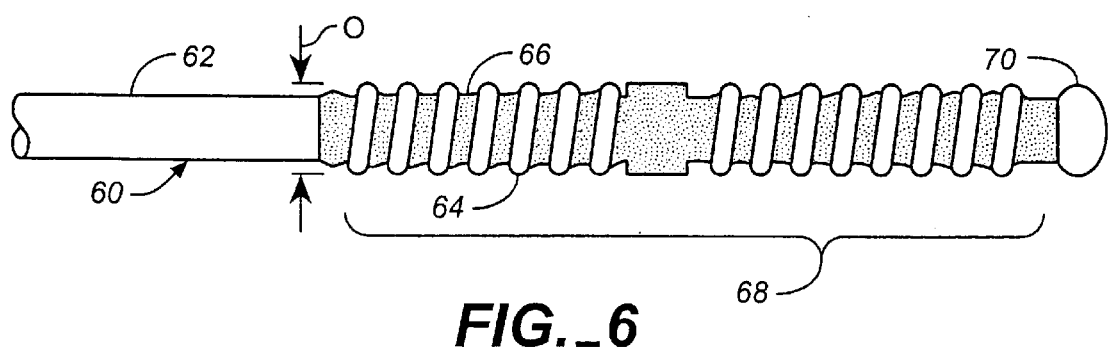
FIG._6

GUIDEWIRE-OCCLUDED BALLOON CATHETER

CROSS-REFERENCE TO RELATED APPLICATIONS

This application claims priority under 35 U.S.C. §§119 and/or 365 to U.S. Provisional Application No. 60/118,390, filed on Feb. 1, 1999; the entire content of which is hereby incorporated by reference.

BACKGROUND OF THE INVENTION

1. Field of the Invention

The invention relates to balloon catheters in which an inflation medium is used to inflate a balloon at a distal end of the catheter.

2. Description of Related Art

Catheters are known in the art and have wide medical applications. Among these applications is the infusion of fluids, medicaments and other material into the body of the patient, or the application of mechanical force such as through dilatation in constricted vessels during angioplasty. The latter procedure is best performed using balloon catheters, wherein a balloon formed on the distal end of the catheter is inflated when the catheter reaches the targeted constriction to thereby apply the requisite mechanical force to case vessel dilation.

Catheters are typically directed to the target site using guidewires, which are generally, smaller and more maneuverable. Once the guide wire is moved to the target location, the catheter is then fed over it to the target location, and therapy commences.

Balloon catheters have been constructed to have dedicated lumens for infusion, guidewire support and supply of inflation fluid to the balloon. In this manner the complexity and size of the device can be reduced, providing critical advantages when small and tortuous vessels are to be navigated.

BRIEF SUMMARY OF THE INVENTION

In accordance with the invention, a catheter is provided with a lumen which serves the dual, alternate functions of supporting a guidewire or draining an inflating fluid from a balloon disposed at the distal end of the catheter. The dual functions are achieved by providing the lumen with a constricted portion forming an inflation seal which contacts a selected portion of the guidewire and forms a seal therewith when the guidewire is properly positioned in the lumen. A change in this relative positioning permits fluid flow through inflation seal and lumen, resulting in drainage of the balloon.

For optimum performance, it is contemplated that at least the inflation seal is formed of a soft material, such as Polyolefin elastomer Engage 8440 having a durometer rating material Hardness, Shore A89. The selected softness of this material enables the inflation seal to be formed with an inner diameter (ID) of the same dimension as the outer diameter (OD) of a coated section of the guidewire without significantly impeding movability of the guidewire therethrough, while at the same time maintaining a fluid-tight seal which enables the balloon to engorge with inflating fluid and thereby inflate. In designing the catheter, account may be taken of the makeup of the guidewire, which guidewire may include a hydrophilically coated coil segment. The hydrophilic coating, when hydrated during use, may undergo swelling, which will impact the interaction between the guidewire and the inflation seal in the lumen since it is contemplated that the guidewire-inflation seal interaction will occur at the hydrophilically coated coil segment of the guidewire.

The position of the inflation seal axially along the length of the catheter can be designed with a view to optimizing the flexibility or other characteristics of the catheter. To that end, the inflation seal may be placed in overlapping relationship with the balloon, or it may be placed distally from the balloon terminus, depending on the application.

Typically, catheters are provided with marker bands to enable their visualization, using medical imaging techniques, during their use in the body of the patient. In accordance with the invention, a unique scheme for attaching the marker bands to the catheter is utilized. Specifically, the marker band is integrally formed with the structure of the catheter. In this manner, the marker band will not interfere with the motion of the guidewire or increase the inner diameter of the catheter, as occurs when the marker band is affixed to the inside of the catheter as in some prior art; nor will the marker band increase the outer diameter of the catheter, as occurs when the marker band is affixed—using an adhesive or a shrink material—to the outside of the catheter as in some of the remaining prior art. An additional advantage is a more secure attachment since the marker band is completely surrounded by the catheter material and is integrally formed therewith.

BRIEF DESCRIPTION OF THE SEVERAL VIEWS OF THE DRAWING(S)

Many advantages of the present invention will be apparent to those skilled in the art with a reading of this specification in conjunction with the attached drawings, wherein like reference numerals are applied to like elements and wherein:

FIG. 1 is a schematic view of a catheter in accordance with the invention;

FIG. 2 is a schematic view of a distal portion of the catheter in accordance with the invention;

FIG. 3 is a schematic view of a distal portion of a catheter in accordance with a another embodiment of the invention;

FIG. 4 is a schematic view of catheter having a guidewire in the occluding position in accordance with the invention;

FIG. 5 is a view showing the construction of a catheter in accordance with the invention; and FIG. 6 is a schematic view showing a guidewire used in conjunction with a catheter in accordance with the invention.

DETAILED DESCRIPTION OF THE INVENTION

FIG. 1 shows generally a catheter 20 in accordance with the invention. Catheter 20 comprises a generally tubular, flexible structure 22 having a proximal portion 24 and a distal, implantable portion 26. A main axial lumen 30 extends substantially the entire length of catheter 20, from proximal portion 24 to distal portion 26, and serves to deliver fluid and materials between the two portions of catheter 20. Additionally, lumen 30 operates to support a guidewire (discussed below) used to guide catheter 20 within the vessels of a patient's body. Proximal portion 24 of catheter 20 is provided with a fitting portion 28 for connection with various devices for delivery of materials or for conducting physiological measurement during use of the catheter 20. Distal portion 26 of catheter 20 is tapered at the end to facilitate insertion and manipulation in the body of the patient. Distal portion 26 is further provided with an inflatable balloon 40 which can serve many functions, including a dilatation function during angioplasty procedure or to assist in the guidance of the catheter 20 to the target site in the body of the patient.

As seen in FIG. 2, balloon 40 is preferably formed of a circumferentially sealed extruded tube or other sheet material 46 forming a sealed cavity 48 over the generally tubular structure 22 of catheter 20. The material of balloon 40 is preferably isoprene or derivatives thereof such as those sold under the trade names of ChronoPrene or Kraton. Main axial lumen 30 is in fluid communication with cavity 48 of balloon 40 through inflation holes, or ports 42. In this manner fluid from a supply reservoir (not shown) exterior of the patient is conveyed-via lumen 30 and ports 42 into cavity 48 for inflation of balloon 40. At a region generally distal of balloon 40, lumen 30 is shown to constrict, such that its inner diameter decreases substantially to form an inflation seal 50 having an inner diameter D. The inflation seal 50 can extend the rest of the length of lumen 30, or it can be of limited relative axial length (see FIG. 4). Although shown in FIGS. 2 and 4 to be distal to balloon 40, inflation seal 50 can also be disposed within balloon 40, as shown in FIG. 3. Formation of the inflation seal 50 within the region of the balloon 40 can provide advantages such as added structural support to the catheter 20 in the region of balloon 40, especially if the seal continues for the remainder of the length of the catheter, as shown in FIG. 3.

Catheter 20 is provided with one or more radioplaque marker bands 32, preferably at the distal portion 26 in the vicinity of balloon 40. Marker bands 32 facilitate visualization of the catheter during operation. In the preferred embodiment, marker bands 32 are integrally formed with the body of the catheter 20, with the material of the generally tubular structure 22 completely enveloping the marker bands in order to eliminate the "footprint" of these bands. In this manner, the bands do not increase the external diameter of the generally tubular structure 22, nor do they unduly constrict main axial lumen 30. To accomplish this arrangement, marker bands 32 can be interposed between layers of the same or different materials used to construct generally tubular structure 22 of catheter 20, as show in FIG. 5, in which 21 designates a first layer of material, 23 designates a second layer of material, and 25 designates a shrink tube material.

Catheter 20 is adapted to receive therein a guidewire 60 such as that shown in FIGS. 4 and 6. Guidewire 60 comprises a core component 62 and a helically wound coil component 64 wound around a distal portion of the core component. The portion of the guidewire 60 containing the coil 64, herein referred to as the coil segment 68, is provided with a hydrophilic coating 66 in order to enhance the lubriciousness of the guidewire 60 and facilitate its movement through the vessel of a patient. The coating is expansible, such that contact with fluid causes absorption of the fluid and expansion of the coating. A solder ball 70 or other blunt surface is provided to prevent the guidewire from damaging the catheter 20 or patient tissue.

In the arrangement in accordance with the invention, inner diameter D (FIG. 2) of inflation seal 50 of catheter 20 is designed to be substantially dimensionally equivalent to the outer diameter O (FIG. 6) of coil segment 68, but without hindering relatively unobstructed axial movement of guidewire 60 in lumen 30. In this manner, a fluid-tight seal can be formed when coil segment 68 of guidewire 60 positioned within inflation seal 50 and fluid is present in balloon 40, illustrated in FIG. 4. The fluid-tight seal is especially effective due to the positive fit of the helically wound coil component 64 and the expansible hydrophilic coating 66, which expands upon absorption of fluid relied upon to inflate balloon 40, within the inflation seal 50. In this manner, when coil segment 68 is present in inflation seal 50, fluid introduced through lumen 30 accumulates in cavity 48 of balloon 40, causing the balloon to inflate. Removal of coil segment 68 from inflation seal 50, by for example axial advancement or retraction of guidewire 60 in lumen 30, then permits drainage of fluid, through inflation seal 50, and deflation of balloon 40. Because radioplaque marker bands 32 are formed integrally in catheter 20 as discussed above, the dimensions of catheter 20 and lumen 30 formed therein are unaltered by the addition of the marker bands 32, further reducing impediments to the free movement of the guidewire 60 in lumen 30.

In order to enhance the sealing qualities of inflation seal 50 without impeding the movability of guidewire 60 therethrough, a suitable, relatively soft material is selected for the inflation seal. Polyolefin elastomer Engage 8440 having a durometer rating material Hardness, Shore A89 is one candidate material.

The above are exemplary modes of carrying out the invention and are not intended to be limiting. It will be apparent to one of ordinary skill in the art that modifications thereto can be made without departure from the spirit and scope of the invention as set forth in the following claims.

What is claimed is:

1. A catheter adapted to support a guidewire having a helically wound coil component and an expansible coating formed thereon, the catheter comprising:

a generally tubular structure having a proximal portion in fluid communication with a distal portion through an axial lumen extending between the proximal and distal portions;

an inflatable balloon disposed at the distal portion in fluid communication with the axial lumen; and a constriction of the axial lumen, the constriction forming an inflation seal adapted to interact with the helically wound coil component and the expansible coating of the guidewire to thereby form a fluid-tight seal between the guidewire and the generally tubular structure.

2. The catheter of claim 1, wherein the constriction is disposed in a region within the balloon.

3. The catheter of claim 1, wherein the constriction is disposed distally of the balloon.

4. The catheter of claim 1, wherein the constriction is formed of a relatively soft material enhancing the interaction with the expansible coating of the guidewire.

5. The catheter of claim 1, further comprising at least one radioplaque marker formed integrally within the tubular structure.

6. The catheter of claim 1, wherein the balloon is formed of isoprene or derivatives thereof, selected from the group consisting of ChronoPrene and Kraton.

7. The catheter of claim 1, further comprising:

one or more marker bands integrally formed in the generally tubular structure.

* * * * *